United States Patent [19]

Johnson et al.

[11] 4,164,225
[45] Aug. 14, 1979

[54] SURGICAL SUTURING INSTRUMENT

[75] Inventors: Alfred A. Johnson, New York; Arthur Zimmet, Huntington, both of N.Y.

[73] Assignee: Johnson & Lorenz, Inc., New York, N.Y.

[21] Appl. No.: 865,221

[22] Filed: Dec. 28, 1977

[51] Int. Cl.² ............................................. A01B 17/04
[52] U.S. Cl. .................. 128/334 R; 128/340; 227/19
[58] Field of Search ............... 128/321, 326, 330, 340, 128/334 R, 339, 346; 29/268, 278; 227/19, 144; 223/102, 104

[56] References Cited

U.S. PATENT DOCUMENTS

| | | | |
|---|---|---|---|
| 1,449,087 | 3/1923 | Bugbee | 128/340 |
| 3,090,386 | 5/1963 | Curtis | 128/334 R |
| 3,470,875 | 10/1969 | Johnson | 128/334 R |
| 3,807,407 | 4/1974 | Schweizer | 128/334 R |
| 3,842,840 | 10/1974 | Schweizer | 128/334 R |
| 3,901,244 | 8/1975 | Schweizer | 128/334 R |

FOREIGN PATENT DOCUMENTS

| | | | |
|---|---|---|---|
| 662602 | 6/1938 | Fed. Rep. of Germany | 128/340 |
| 138326 | 5/1960 | U.S.S.R. | 128/334 R |

Primary Examiner—Edgar S. Burr
Assistant Examiner—James R. Feyrer
Attorney, Agent, or Firm—Cooper, Dunham, Clark, Griffin & Moran

[57] ABSTRACT

A surgical suturing instrument including a first jaw carrying a capsule which contains a suture having needles attached to its ends, a second jaw for receiving the needles and cooperating with the first jaw to clamp tissue to be sutured, a plunger in the first jaw for transferring the needles from the capsule to the second jaw through the clamped tissue, an actuator arm for successively moving the first jaw to closed position and operating the plunger, a common pivotal mounting for the jaws and the arm, and a latch member pivotally mounted on the first jaw for selectively interconnecting the first jaw with the arm and with the second jaw in succession as the arm is moved in a jaw-closing direction, so that such movement of the arm first closes the jaws and thereafter operates the plunger while the jaws are interlocked. The capsule has a notched bobbin for holding a U-shaped suture with the bight of the suture received in the notch. The second jaw has apertures for receiving the needles and retaining them, by interference, against withdrawal.

12 Claims, 21 Drawing Figures

SURGICAL SUTURING INSTRUMENT

BACKGROUND OF THE INVENTION

This invention relates to surgical suturing instruments. More particularly, it relates to instruments having jaws for successively clamping and suturing a portion of body tissue in an essentially unitary manipulative operation, wherein the suture to be applied is carried in one of the jaws and passed therefrom through the tissue while the jaws are clamped.

In a specific sense, the invention is directed to improvements in suturing instruments of the general type specifically exemplified by illustrative embodiments described in U.S. Pat. No. 3,807,407. That patent discloses a suturing instrument comprising a pair of pivotally interconnected jaws, one of which carries a flexible suture with a pair of needles attached to the suture ends, and contains a plunger for transferring the needles to the second jaw through a portion of body tissue clamped between the jaws. The second jaw has a pair of apertures for receiving and frictionally retaining the needles and is provided with a handle. An actuator arm, mounted on the same pivot as the two jaws, is connected to the plunger; and means are provided for selectively interconnecting the first jaw with the actuator arm and with the second jaw in succession during progressive closing movement of the actuator arm and the handle of the second jaw. The actuator arm and the second-jaw handle are disposed to be grasped by the thumb and fingers of the user's hand and to be manipulated in forceps-type opening and closing action.

In the use of this instrument, in the initial stage of closing movement of the arm and handle, the arm (being maintained in fixed relation to the first jaw by the interconnecting means) swings the first jaw into a closed or clamping position relative to the second jaw. At that point, the first jaw becomes disconnected from the actuator arm and interlocks with the second jaw so as to be held in fixed relation to the second jaw during further closing movement of the arm. Since the arm is now no longer fixed in relation to the first jaw, such further closing movement of the arm advances the plunger within the first jaw, forcing the needles through a portion of tissue clamped between the jaws and into the needle-receiving apertures of the second jaw. Upon re-opening of the instrument, the needles (being retained in the second jaw) draw the suture through the tissue; the needles may then be clipped off and removed, and the free ends of the suture may be tied.

An advantage of the described instrument is that the clamping pressure exerted on the tissue between the jaws is limited by the interlocking of the jaws; thus, the plunger-operating movement of the actuator arm (after the tissue has been initially clamped) cannot cause excessive compression of the clamped tissue. Also, the plunger cannot be operated until the actuator arm is disconnected from the first jaw, as is desired to prevent discharge of the needles from the first jaw until the second jaw is positioned to receive them. The structures heretofore proposed for use as the interconnecting means of such an instrument, however, have relied on spring forces to maintain the interconnection at least between the first jaw and the actuator arm. The spring or springs employed to exert these forces are subject to failure through fatigue; moreover, if the tissue to be clamped and sutured is tough or resistant to compression, the spring forces may yield prematurely and the actuator arm may then move the plunger to discharge the needles while the jaws are still partially open, with the result that the suture is not applied because the needles do not enter the receiving apertures of the second jaw. In such case, difficulty and inconvenience as well as loss of valuable time may attend the location and removal of the discharged needles.

In addition, in arrangements heretofore proposed for the needle-receiving apertures, the needles are withdrawn from the apertures through the same openings they enter when transferred from the first jaw. In some instances, upon opening of the instrument after the needles have been transferred, passage of the suture through the tissue may be sufficiently hindered or retarded to cause premature withdrawal of the needles from the apertures, again occasioning inconvenience and difficulty.

In one embodiment of the instrument described in the above-cited patent, the suture, together with its needles, is contained in a capsule removably mounted in the first jaw so that after the suture is used, the empty capsule may simply be discarded and replaced with a fresh suture-containing capsule, i.e. enabling immediate application of a second suture. Within the capsule, the central portion of the suture is wound on a bobbin, while the needles (attached to the suture ends) are positioned for engagement with the plunger and for discharge by the plunger through the clamped tissue and into the second-jaw apertures. For proper suturing action, it is important that the two ends of the suture be withdrawn at the same rate from the capsule as the instrument is re-opened; however, in embodiments of the bobbin heretofore proposed, it has been possible for the suture to be nonuniformly wound, i.e. so that the two ends are not paid out evenly. Such uneven discharge of the two suture ends hinders proper functioning of the instrument.

Another form of the instrument described in the above-cited patent is adapted to apply staples rather than flexible sutures (e.g. filaments or threads). These staples are contained in a magazine or capsule in the first jaw and are forced through a clamped portion of body tissue by the plunger, being bent by a facing surface of the second jaw so as to grip the tissue. As used herein, the term "suture" embraces such staples as well as flexible sutures.

SUMMARY OF THE INVENTION

The present invention broadly contemplates the provision of improvements, especially for enhancing reliability of performance, in a surgical instrument of the type including first and second tissue-clamping jaws, the second jaw having a handle; an actuator arm manipulable jointly with the handle; means for pivotally interconnecting the jaws and arm for movement about a common axis; suturing means carried by the first jaw, including an element operable by movement of the arm relative to the first jaw for applying a suture to tissue clamped between the jaws; and latch means for selectively interlocking the first jaw with the arm and with the second jaw in succession during progressive movement of the arm in a closing direction toward the handle, so that such movement of the arm initially moves the first jaw to a closed or clamping position (relative to the second jaw) at which the jaws interlock, and thereafter operates the suture-applying element.

In such an instrument, the invention in one specific aspect contemplates the provision, as the latch means, of a latch member pivotally mounted on the first jaw and having first and second portions respectively engageable with the arm and with the second jaw, the first portion serving to interlock the arm and first jaw and to transmit motion from the arm to the first jaw when the first jaw is out of closed position, and the second portion being engaged by the second jaw for pivoting the first portion out of motion-transmitting engagement with the arm as the first jaw reaches the closed position. Consequently, the arm is released for movement relative to the first jaw (enabling operation of the suture-applying element) only upon proper positioning of the two jaws for suture application, i.e. because such release is effected by an interengagement of the latch member and the second jaw that can occur only when the first jaw arrives at the closed position; hence premature discharge of the suture is positively prevented.

The latch member of the invention is a rigid, effectively unitary body, having (on its first portion) a surface disposed to be engaged by an abutment formed on the arm, the last-mentioned surface and the arm abutment being mutually so disposed that the abutment bears against the surface, and transmits jaw-closing force to the latch member (and thus to the first jaw) in a direction tending to oppose pivotal motion of the latch member out of such motion-transmitting engagement with the arm. The second portion of the latch member has a projection disposed for engagement by an abutment formed on the second jaw, as the first jaw approaches the closed position, such that closing of the jaws pivots the latch member as described above. The aforementioned surface of the first portion of the latch member is arcuate, permitting the arm abutment to slide therealong as the latch member begins to pivot, and is of such extent that the arm abutment disengages therefrom when the latch member has pivoted to an orientation corresponding to arrival of the first jaw at the closed position. In addition, the configuration of the latch member is such as to hold the first jaw in fixed, interlocked relation to the second jaw after the first jaw reaches closed position while permitting further movement of the actuator arm in a closing direction for operating the suture-applying element.

As a further particular feature of the invention, in embodiments for applying a flexible suture having one or more needles attached thereto and initially carried by the first jaw, the second jaw is provided with one or more needle-receiving apertures of novel configuration for preventing undesired release or withdrawal of the needle or needles during re-opening of the instrument, i.e. after the needle or needles have been transferred to the second jaw. Each such aperture is dimensioned to receive a short, straight needle connected to the suture, and is disposed for alignment with the path of needle advance from the first jaw, having a first opening through the surface of the second jaw facing toward the first jaw, and a second opening opposed to the first opening. The second jaw has a ledge portion, facing away from the first jaw, extending laterally from at least one side of the second opening of each aperture. When the jaws are closed, operation of the suture-applying element (which may, for example, be a plunger having a forward extremity engaging the rearward end of a needle in the first jaw) advances the needle entirely through the receiving aperture of the second jaw so that the rearward end or base of the needle emerges through the second opening of the aperture. As this happens, the needle immediately becomes misaligned with the aperture; i.e. the base of the needle moves laterally of the aperture opening as it emerges therethrough, and engages the adjacent ledge portion of the second jaw. Interference between the ledge portion and the needle base prevents subsequent withdrawal of the needle from the aperture, as the instrument is reopened, regardless of the pull exerted on the needle by the suture.

A still further feature of the invention, in embodiments wherein a flexible U-shaped suture having a pair of needles respectively attached to its ends is carried in a capsule mounted in the first jaw, resides in the provision of a special bobbin for the suture within the capsule. This bobbin, supported for rotation, has side flanges and an intermediate septum, parallel to the flanges, with a notch formed in the septum. When the U-shaped suture is wound on the bobbin, the bight of the "U" is placed within the notch, and the two legs of the suture are respectively wound on the bobbin on opposite sides of the septum, leading forwardly from the bobbin to the needles. In this way, the portions of the two legs wound on the bobbin are prevented from crossing each other, so that as the suture is withdrawn from the bobbin, neither leg hinders the movement of the other. Thus the bobbin structure of the invention assures that both legs of the suture are paid out evenly.

Further features and advantages of the invention will be apparent from the detailed description hereinbelow set forth, together with the accompanying drawings.

DETAILED DESCRIPTION

Figure 1:
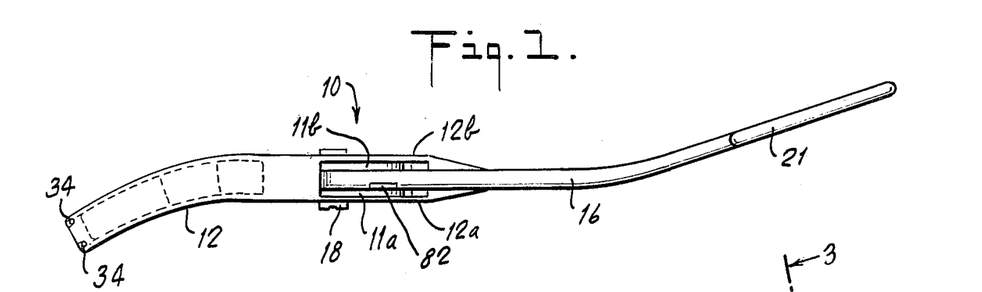
FIG. 1 is a plan view of a surgical suturing instrument embodying the present invention in a particular form.
Figures 2, 3, 4, 5:
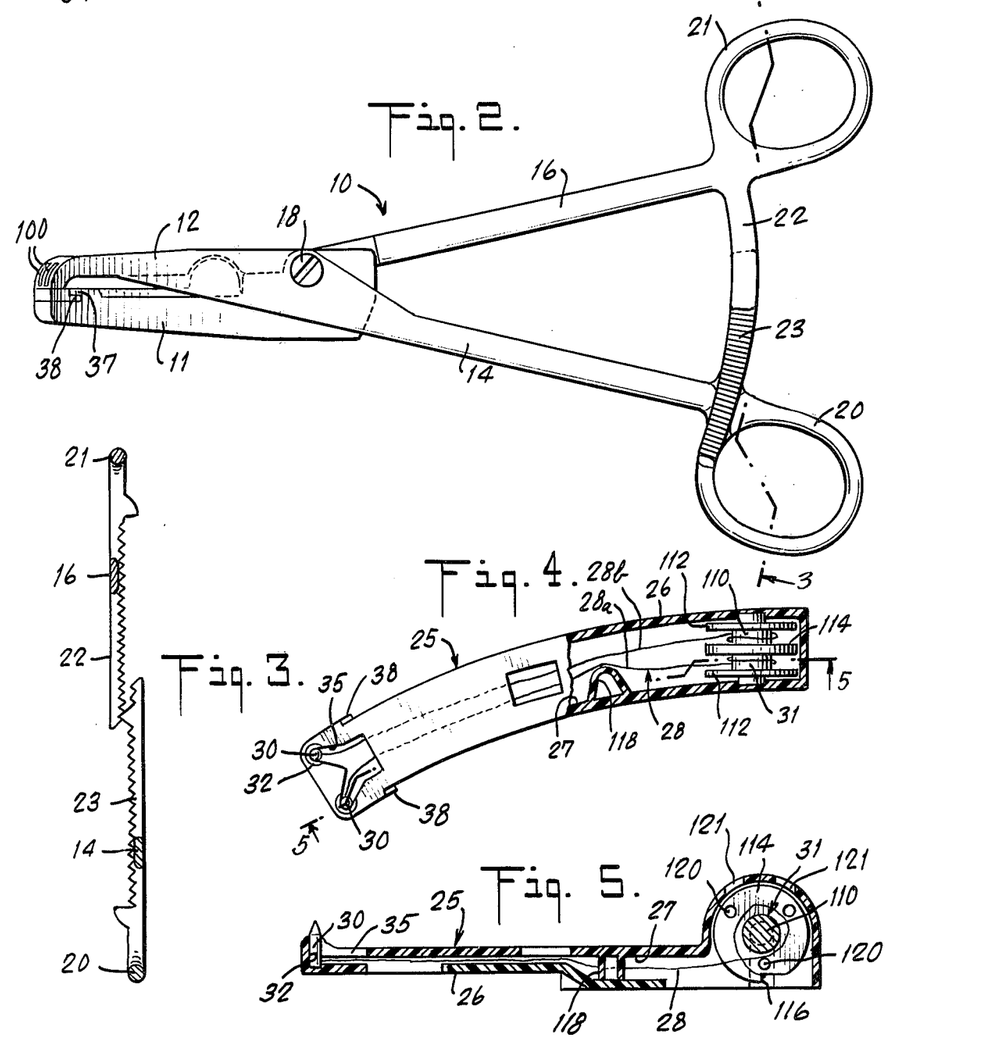
FIG. 2 is a side elevational view of the instrument of FIG. 1.
FIG. 3 is a view taken along the line 3—3 of FIG. 2.
FIG. 4 is an enlarged plan view, partly in section, of a suture-containing capsule incorporated in the instrument of FIG. 1.
FIG. 5 is a sectional elevational view of the capsule, taken along the line 5—5 of FIG. 4.

Referring to the drawings, the invention is illustrated as embodied in a suturing instrument 10 (FIGS. 1 and 2) comprising a first jaw 11, a second jaw 12 having a handle 14 formed integrally therewith, and an actuator arm 16, all fabricated of stainless steel or the like. The jaws and arm are pivotally interconnected, for relative angular movement about a common axis, by means of a pivot pin 18 which extends through the rearward portion of jaw 11, the forward portion of arm 16, and an intermediate locality of jaw 12, so that the two jaws extend forwardly from the pivot pin for clamping a portion of body tissue while the arm and handle extend rearwardly from the pivot pin for manipulation by a user, i.e. in the manner of a forceps. The handle 14 and arm 16 are respectively adapted to be grasped by the thumb and finger of a user's hand, and to this end are provided with conventional finger grips 20 and 21; also as in a conventional forceps, the arm and handle bear inwardly projecting ratchet members 22 and 23 which overlap for interengagement (FIG. 3). To enhance visibility of the forward tip of the instrument during use, the jaws may be curved laterally ahead of the pivot pin (as best seen in plan view, FIG. 1) while the arm and handle are curved in a reverse direction rearwardly of the pivot pin.

The jaw 11 is adapted to receive a removable suture-carrying capsule 25 (FIGS. 4 and 5) comprising an elongated, molded plastic housing 26 which, in the illustrated embodiment, is curved to conform to the jaw curvature and which defines a recess 27 for containing an elongated flexible suture 28 having a pair of short needles 30 respectively secured to its two ends. The central portion of the suture is wound on a bobbin 31 rotatably mounted in the capsule at the rearward end of the recess 27, and the two legs of the suture extend forwardly therefrom through the recess. At the forward end of the capsule, the two needles are respectively disposed in two parallel needle-holding channels 32, extending transversely of the long dimension of the capsule and open at each end (i.e. through the base and top of the capsule), the needles being retained frictionally by tightness of fit of their base portions in the channels. The channels 32 are so positioned and oriented that, when the capsule is mounted in the jaw 11 and the two jaws of the instrument are closed, the forward ends of the needles are respectively positioned within openings of needle-receiving apertures 34 formed in the forward of the second jaw 12. A generally Y-shaped opening 35 in the forward portion of the top of the capsule, extending from the recess 27 to the needle-holding channels 32, permits the suture to be completely withdrawn from the capsule when the needles are discharged from the capsule as hereinafter described.

As best seen in FIGS. 6-9, 11, 15, 20 and 21, the jaw 11 has an elongated recess 36 (opening toward the jaw 12) for receiving and snugly holding the capsule 25. The side walls of the jaw defining this recess have, in their forward portions, upwardly and forwardly projecting lugs 37 which mate with corresponding lugs 38 molded on the side walls of the capsule to ensure retention and proper positioning of the capsule when the capsule is press-fitted into the recess 36.

Also mounted in the jaw 11 is a suture-applying element comprising an elongated, flexible plunger 40 (FIG. 19) which terminates at its forward extremity in a head 41 bearing a pair of inwardly curved prongs 42 respectively adapted to engage the bases of a pair of needles 30 within the needle-holding channels of a capsule 25. The plunger extends beneath the jaw recess 36 (and thus beneath the capsule 25) along the full length thereof, in a passage 44 defined between the outer body of the jaw 11 and an insert member 45 fixedly secured within the jaw body. Passage 44 is constructed to permit longitudinal (i.e. forward and rearward) movement of the plunger therein, and to this end its forward portion is enlarged to accommodate such movement of the head 41. This forward portion of the passage opens into recess 36 to enable the plunger prongs to engage the needles contained in a capsule disposed in the latter recess.

The rearward extremity of the plunger 40 extends rearwardly beyond the passage 44 into an open space 46 defined within the rear portion of jaw 11, and terminates in a short transverse bar 48. The forward end of the actuator arm 16 includes a projection 50 extending from the pivot pin 18 into the space 46 for engaging the bar 48 of plunger 40; as shown, bar 48 is received in a notch 51 formed in projection 50. The space 46 is dimensioned to permit pivotal movement of the arm 16 about pin 18 relative to jaw 11, in a plane parallel to the direction of longitudinal movement of the plunger; by virtue of the above-described connection or interengagement between projection 50 and bar 48, such pivotal movement of arm 16 relative to jaw 11 moves the plunger forwardly and rearwardly within the jaw.

The operation of the instrument 10 may now be generally understood, with reference to FIGS. 6-10. Prior to use of the instrument, a capsule 25 containing a suture 28 and needles 30 is inserted in the recess 36 of jaw 11. The handle 14 and arm 16 are grasped by the thumb and fingers of the user's hand. With the jaws open (and the handle and arm correspondingly divergent), the forward tip of the instrument is positioned adjacent a portion 52 of body tissue to be sutured. The arm and handle are then brought progressively together, in forceps-closing action.

By means hereinafter to be described, and incorporating important features of the present invention, the first jaw 11 is selectively interlocked, in succession, with the arm 16 and with the second jaw 12 during the course of progressive movement of the arm 16 in a closing direction, i.e. toward the handle 14. Thus, when the jaws are open, the arm 16 is fixed in relation to the jaw 11, which is free to pivot relative to the jaw 12. At this time, and as long as the arm and jaw 11 remain interlocked, the projection 50 is at the rearward end of space 46; hence the plunger 40 is, and remains, fully retracted.

Figure 6:
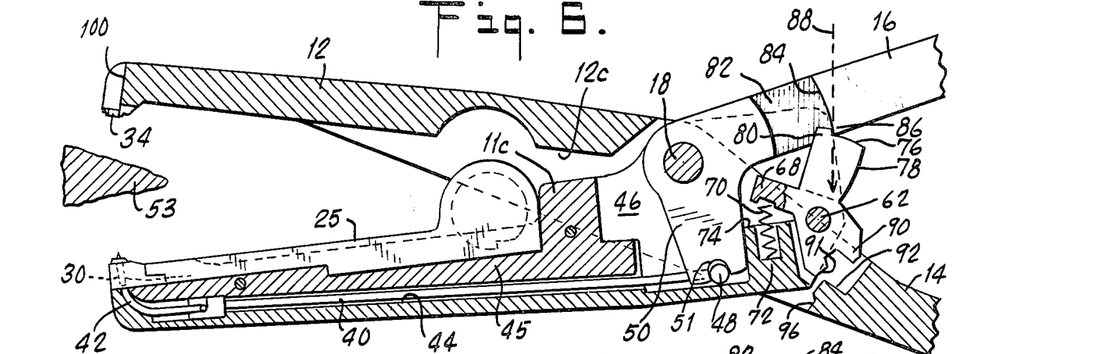
FIGS. 6 and 7 are enlarged sectional side elevational views of the forward portion of the instrument of FIG. 1, illustrating successive stages in the closing of the jaws of the instrument.
Figure 7:
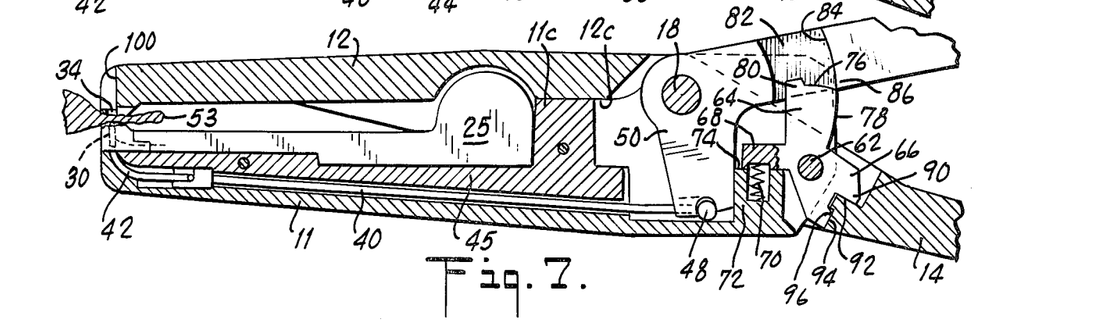

Because the jaw 11 and the arm are interlocked, manipulation of the arm and handle to pivot the arm in a closing direction toward the handle causes progressive closing movement of the jaws (FIG. 6), until the jaw 11 reaches a fully closed, clamping position relative to the jaw 12 (FIG. 7). In the fully closed position, the forward tips of the jaw 12 and of the capsule 25 in jaw 11 are in register, and are closely adjacent each other, clamping the tissue 53 between them.

Figure 8:
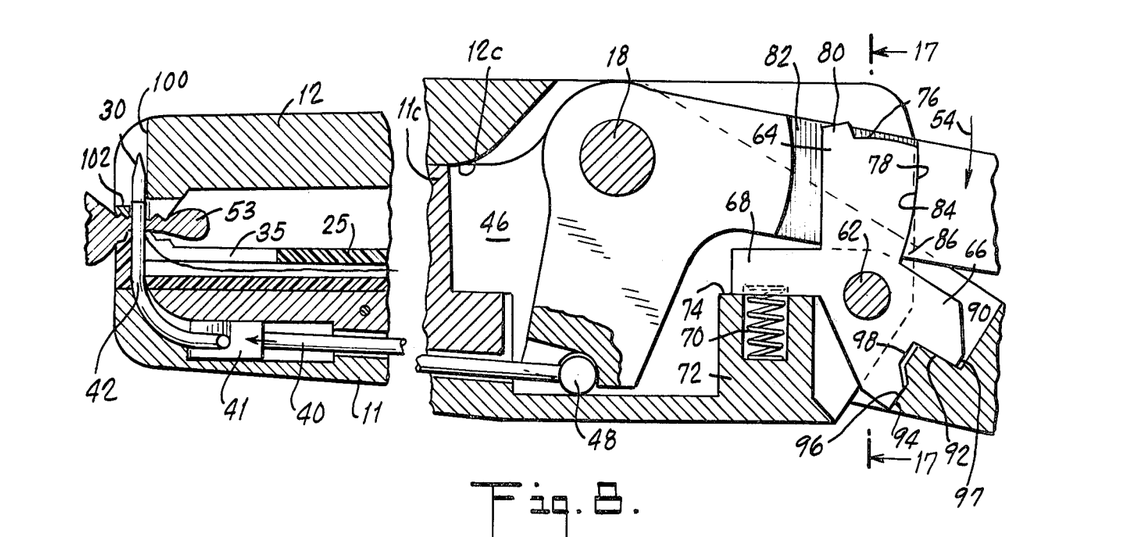
FIG. 8 is a further enlarged, fragmentary sectional view of the portion of the instrument shown in FIGS. 6 and 7, illustrating the transfer of the needles from the capsule to the second jaw of the instrument.

Upon arrival of the jaw 11 at the fully closed position of FIG. 7, the aforementioned interlocking means functions to unlock the jaw 11 from the arm 16, and simultaneously to interlock the jaw 11 to the jaw 12. Arm 16 is now free to pivot about pin 18 relative to jaw 11 as it is moved further in the closing direction (represented by arrow 54 in FIG. 8), and such further closing movement of the arm neither changes the relative position of the jaws nor exerts additional pressure on the clamped tissue 53. Instead, the further closing movement of arm 16 swings its projection 50 forwardly in space 46 (i.e. relative to jaw 11), advancing the plunger 40 within jaw 11 until the plunger prongs engage the needles 30. The prongs force the needles from the capsule through the clamped tissue 53 and into the needle-receiving apertures 34 in jaw 12 (as shown in FIG. 8), where the needles are retained as hereinafter described. It may be explained that the forward ends of the needles project out of the capsule sufficiently so that, when the jaws reach fully closed position, these forward ends pierce the clamped tissue and enter the openings of the apertures 34, i.e. even before the needles are discharged from the capsule; this arrangement ensures full positional control of the needles at all times. Until the needles are discharged, however, they are held by the capsule so that if the instrument is opened, they remain in the capsule.

The instrument is then manipulated to move the arm 16 in an opening direction relative to handle 14. Initially, while jaws 11 and 12 remain interlocked, such opening movement of the arm retracts the plunger 40 back to its starting position. Upon further opening movement of the arm 16, the interlocking means unlocks the jaws and couple jaw 11 again to arm 16, so that the opening of the arm and handle opens the jaws, releasing the tissue 53. As this occurs (FIG. 9), the retention of the needles in the jaw 12 draws the suture 28 out of the capsule and through the tissue. The ends of the suture are clipped and tied (FIG. 10); the needles are removed from jaw 12; and the empty capsule 25 is replaced with a fresh capsule for application of the next suture.

Figure 10:
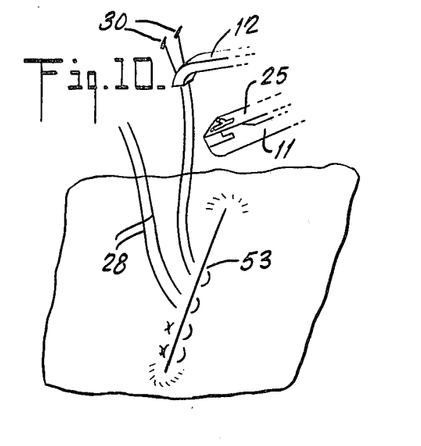
FIG. 10 is a simplified perspective view further illustrating the operation of the instrument in applying a succession of sutures.
Figure 11:
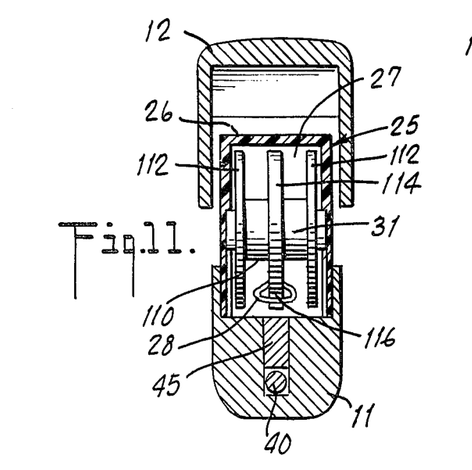
FIG. 11 is a sectional view taken along the line 11—11 of FIG. 9.

In this way, a suture may be applied with an essentially unitary closing and opening manipulation of the instrument 10, which successively clamps the tissue to be sutured and passes the suture therethrough. Use of the replaceable capsules, preloaded with sutures and needles, facilitates rapid application of a succession of sutures, as shown in FIG. 10.

Figures 15, 16, 17, 18, 19, 20:
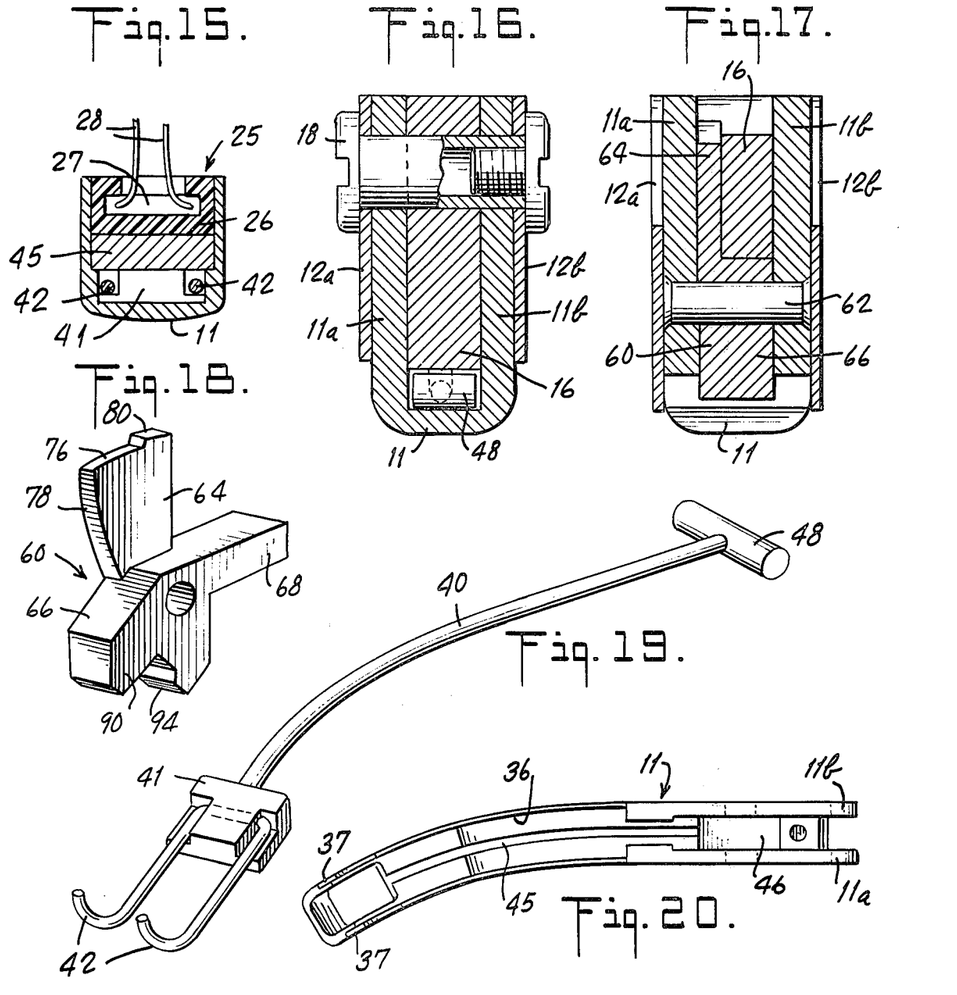
FIG. 15 is a sectional view taken as along the line 15—15 of FIG. 9.
FIG. 16 is a sectional view taken as along the line 16—16 of FIG. 9.
FIG. 17 is a sectional view taken as along the line 17—17 of FIG. 8.
FIG. 18 is an enlarged perspective view of the latch member of the instrument of FIG. 1.
FIG. 19 is an enlarged perspective view of the suture-applying element of the instrument of FIG. 1.
FIG. 20 is a plan view of the first jaw of the FIG. 1 instrument.
Figure 21:
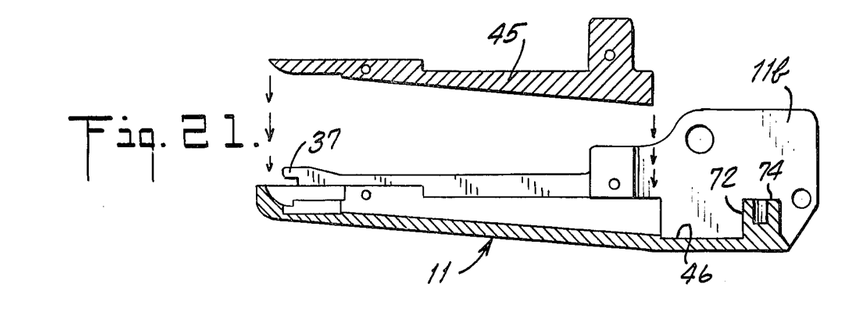
FIG. 21 is an exploded elevational sectional view of the jaw shown in FIG. 20.

By way of further explanation of the structure of the instrument 10, it may be noted that at the locality of pivot pin 18, the jaw 12 is bifurcated into two lateral wall portions 12a and 12b which merge into the handle 14 rearwardly of the pivot pin. The rearward portion of jaw 11 (i.e. the portion defining space 46) is interposed between these wall portions 12a and 12b, as shown in FIGS. 16 and 17, and is itself U-shaped, having spaced parallel side walls 11a and 11b between which the arm 16 is interposed. Pin 18 thus extends successively through wall portion 12a, wall 11a, arm 16, wall 11b, and wall portion 12b.

As thus far described, the instrument 10 corresponds generally to devices shown in the aforementioned U.S. Pat. No. 3,807,407. The present invention, as embodied in the instrument 10, resides in the incorporation therein of features of arm and jaw interlocking means, capsule structure, and needle-receiving aperture structure, now to be set forth in detail.

Thus, in accordance with a first specific aspect of the invention, and as a particular feature thereof, the jaw 11 bears a latch member 60 which, together with cooperating specially formed portions of the jaws and arm, provides assured, reliable, selective interlocking of the jaw 11 with the arm 16 and with the jaw 12 in succession, in a manner positively preventing premature discharge of the needles 30 from the capsule 25 by the plunger 40. This latch member 60, best seen in FIGS. 6–9, 17 and 18, is a unitary, rigid metal body interposed between the walls 11a and 11b of jaw 11 and pivotally secured thereto by a pin 62 extending between the walls 11a and 11b rearwardly of pin 18, for angular movement about an axis parallel to the axis of rotation about pin 18.

Specifically, the latch member comprises a first portion 64 projecting generally radially of pin 62 for engaging a cooperating portion of the arm 16; a second portion 66 also projecting generally radially of pin 62 for engaging a cooperating portion of the handle 14 of jaw 12; and a third portion 68 again projecting generally radially of pin 62 for engagement by a compression spring 70 which acts between portion 68 and a spring seat 72 formed on the jaw 11 to bias the latch member 60 for rotation about pin 62 in a clockwise direction as seen in FIGS. 6–9. The portion 68 of the latch member also serves as a stop to limit counterclockwise rotation of the member, by engagement with a facing stop surface 74 of the spring seat 72.

The first portion 64 of the latch member 60 has a first outwardly facing arcuate edge surface 76 with an axis of curvature coincident with the axis of rotation about pin 62, and a second, rearwardly facing arcuate edge surface 78 that extends from the rearward extremity of surface 76 toward the pin 62. Surface 78 is so formed that, when latch member portion 68 abuts the stop surface 74, the axis of curvature of surface 78 coincides with the axis of rotation about pin 18. A short outwardly projecting stop 80 is formed at the forward end of surface 76.

In the forward portion of the arm 16, but rearwardly of pin 18, there is formed a groove 82 for receiving latch member portion 64. The rear wall of groove 82 is an arcuate ledge 84 having an axis of curvature coinciding with the axis of rotation about pin 18, and a radius of curvature substantially the same as that of the latch member surface 78. Arm 16 and latch member 60 are so disposed that, when the latch member is pivoted clockwise away from engagement with stop surface 74 by the spring 70, as shown in FIG. 6, surface 76 interferes with the inner extremity 86 of ledge 84 thereby preventing clockwise angular movement of arm 16 about pin 18 relative to jaw 11. The projection 50 of arm 16 is then at the rearward extremity of its range of movement within space 46, and abuts the forward side of spring seat 72 to prevent counterclockwise angular movement of the arm 16 relative to jaw 11. Engagement of stop 80 with ledge 84 limits clockwise movement of latch member surface 76 relative to ledge 84. Thus the jaw 11 and the arm 16 in this disposition are effectively interlocked against relative angular movement about pin 18; in consequence, any angular movement of arm 16 about pin 18 relative to jaw 12 produces a corresponding, equal angular movement of jaw 11 about pin 18 relative to jaw 12 and cannot effect any displacement of the retracted plunger 40 within jaw 11.

The aforementioned extremity 86 of ledge 84, in other words, constitutes an abutment of arm 16 bearing against the surface 76 of the latch member so as to transmit closing motion of the arm to the jaw 11. The direction of the force (represented by line 88 in FIG. 6) thus exerted on the latch member by the arm abutment 86 is tangential to the locus of revolution of the abutment 86 about pin 18, and pin 62 is so disposed that this direction of force always urges the latch member clockwise about pin 62 as seen in FIG. 6; hence the force exerted by the arm on the latch member does not oppose the force of spring 70, and (since clockwise rotation of the latch member relative to the arm is positively limited by stop 80) cannot prematurely disengage the arm from the latch member, e.g. even if closing of the jaws is resisted by interposition of tough, compression-resistant tissue between the jaws. As will therefore be apparent, the interlocking engagement of the arm and jaw 11 is not dependent on any spring forces, but is in the nature of a positive interlock until the jaw 11 reaches its fully closed position relative to jaw 12.

At the rearward extremity of the bifurcated portion of jaw 12, i.e. at the juncture of wall portions 12a and 12b with handle 14, the jaw 12 is provided with an abutment or tooth 90 disposed to engage a projecting finger 92 on the latch member portion 66 as the jaw 11 approaches its closed position relative to the jaw 12. By virtue of this engagement of the tooth 90 with finger 92, continuing closing movement of the interlocked arm 16 and jaw 11 relative to jaw 12 forces the latch member 60 to rotate counterclockwise, against the force of spring 70, until the latch member portion 68 engages the stop surface 74 to prevent further counterclockwise rotation of the latch member. The curvature of the latch member surface 76 permits the latch member to slide relative to the arm abutment 86, during such counterclockwise movement of the latch member, while the relative positions of the arm and jaw 11 remain unchanged. Thus, closing movement of the arm continues to effect closing movement of the jaw 11 (still without advancing the plunger 40) until the latch member abuts the stop surface 74.

Since, as stated above, the radii of curvature of the latch member surface 78 and the ledge 84 are approximately equal (the radius of curvature of the latter being very slightly greater than that of the former), the radial distance of arm abutment 86 from the axis of pivot point 18 is just slightly greater than the radial distance of the rearward extremity of surface 76 from the same axis when the latch member is at the limit of its counterclockwise travel about pin 62, i.e. when the latch member is in the angular orientation (relative to jaw 11) shown in FIGS. 7 and 8. That is to say, the front-to-rear dimension of surface 76 is such, in relation to the radius of curvature of ledge 84, that surface 76 disengages from abutment 86 as the latch member reaches this counterclockwise limiting orientation.

FIG. 7 illustrates the relative positions of the arm, jaws and latch member just as counterclockwise rotation of the latch member is arrested by engagement of portion 68 with the stop surface 74. At this point, the jaw 11 has just arrived at its final, fully closed or clamping position relative to the jaw 12, and the rearward extremity of the latch member surface 76 has just moved out of engagement with the abutment 86 of arm 16, so that the arm and the jaw 11 are no longer interlocked; the arm 16, however, has not yet moved relative to jaw 11, and therefore the plunger 40 is still fully retracted. At the same time, a flat surface 94 on the latch member portion 66 comes into flush engagement with a corresponding surface 96 of jaw 12 immediately outwardly of tooth 90, and facing surfaces of tooth 90 and finger 92 are likewise in flush engagement. It will be noted that the latch member portion 66 is shaped, at localities 97 and 98 (FIG. 8), to provide clearance for rotation of the latch member into and out of such engagement with the tooth 90.

The disengagement of abutment 86 from surface 76 now permits the arm 16 to move angularly relative to the jaw 11, i.e. as the arm is advanced further in the closing direction represented by arrow 54 (FIG. 8) relative to the jaw 12. The arm abutment 86 passes rearwardly of the latch member portion 64, with the curved ledge 84 in sliding engagement with the correspondingly curved latch member surface 78 owing to the above-described relationship of their respective radii of curvature. During such movement of the arm, the jaw 11 is positively locked to the jaw 12, owing to the described engagement of latch member surface 94 with the surface 96 of jaw 12 and the engagement of latch member surface 78 with the ledge 84 of arm 16. Abutment of a portion 11c of jaw 11 with the facing surface 12c of jaw 12 also blocks further jaw-closing movement. Therefore, jaw 11 is held fixed in position relative to jaw 12, assuring maintenance of the needles 30 (in capsule 25) in proper register with the needle-receiving apertures 34 of jaw 12 for transfer of the needles. This movement of arm 16 about pin 18 relative to jaw 11 in the direction of arrow 54, as shown in FIG. 8 and described above, advances the plunger 40 longitudinally in the jaw 11 to force the needles through the clamped tissue 53 and into the apertures 34.

Figure 9:
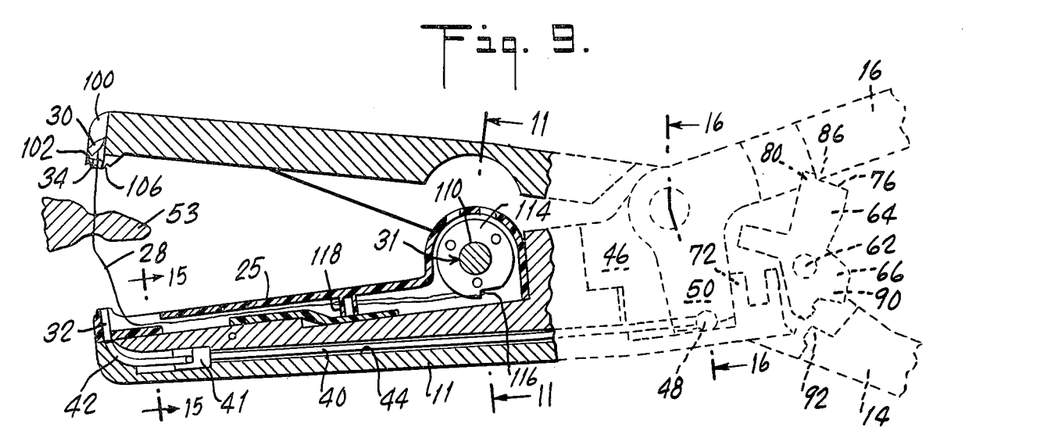
FIG. 9 is a view similar to FIGS. 6 and 7, illustrating the re-opening of the instrument after the needles have been transferred.

As the arm 16 and handle 14 are reopened after transfer of the needles is complete, the projection 50 of arm 16 initially returns to the rearward limit of its travel in space 46, fully retracting the plunger 40, while the jaws remain interlocked by the latch member 60. When the projection 50 again abuts the spring seat 72, it transmits an opening force from the arm 16 to the jaw 11, and since the ledge 84 has now returned to the position shown in FIG. 7 relative to the latch member, i.e. since latch member surface 78 is no longer engaged by the ledge, the latch member is released for clockwise rotation under the force of spring 70, thereby unlocking the jaws. Accordingly, further opening movement of the arm 16 relative to handle 14 moves jaw 11 away from jaw 12, while the latch member surface 76 is returned to engagement with the arm abutment 86, all as shown in FIG. 9. In this way, the jaws are reopened, drawing the suture 28 through the tissue 53.

It will be seen that in the operation of the latch member 60, the spring 70 serves merely as a positioning spring, and does not at any point oppose externally applied forces. Consequently, the possibility of failure resulting from spring fatigue is minimized, and malfunction cannot occur by overriding of the spring forces. The latch member, therefore, provides a positively operating interconnection between the arm and jaws affording high reliability and long performance life under widely varying conditions of use.

Figure 12:
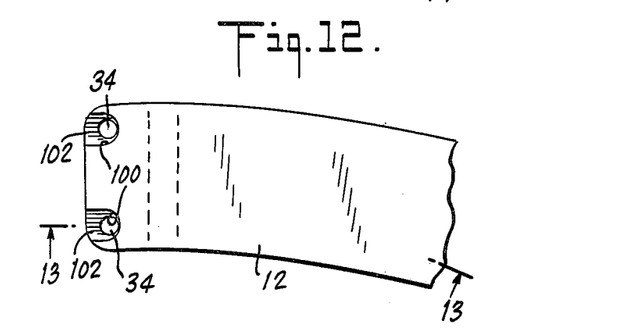
FIG. 12 is an enlarged top plan view of the forward end of the second jaw of the instrument, showing the needle-receiving apertures.
Figure 13:
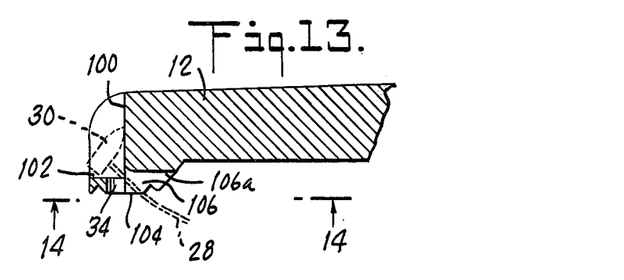
FIG. 13 is a sectional view taken along the line 13—13 of FIG. 12.
Figure 14:
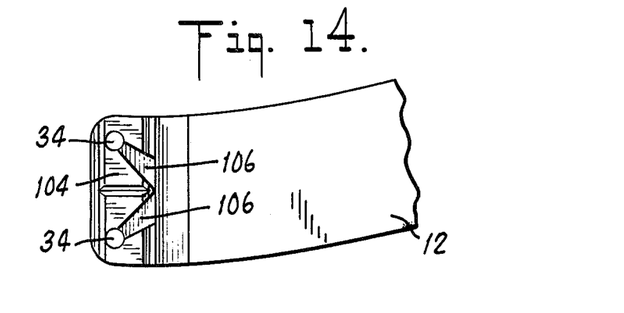
FIG. 14 is a bottom plan view of the second jaw portion shown in FIG. 12, taken as along the line 14—14 of FIG. 13.

Further particular features of the invention are embodied in the needle-receiving aperture structure of the jaw 12, illustrated in FIGS. 12–14. As there shown, a pair of parallel vertical channels 100, each terminating inwardly in a flat outwardly facing ledge or surface 102, are formed in the forward tip of the jaw 12. The needle-receiving apertures 34 respectively open outwardly through the surfaces 102, and extend inwardly therefrom through a head portion 104 of the jaw 12 to open inwardly through the inwardly facing surface of the head portion. It will be understood that the terms "outwardly" and "inwardly," as used with reference to FIGS. 12-14, refer to directions respectively toward and away from the jaw 11.

Each of the apertures 34 is a short cylindrical bore defined by the head portion and having a rear wall essentially continuous with the rear wall of the channel 100 in which the aperture opens. The inwardly facing surface of the head portion 104 is offset inwardly with respect to the body of jaw 12, as best seen in FIG. 13, and has formed therein a pair of diverging, inwardly opening grooves 106 which extend forwardly to communicate, respectively, with the two apertures 34. The grooves 106 are arranged to accommodate the ends of the suture 28 respectively attached to the two needles 30, i.e. as the needles are introduced to the apertures 34 by the action of the plunger 40. To this end, the depth of each groove is such that each surface 102 is offset inwardly with respect to the outer wall 106a of the associated groove 106, i.e. to enable a needle 30 to pass through and beyond the aperture 34 without the necessity of confining both the needle and the attached suture end in the constricted cylindrical opening of the groove.

Typically, each needle 30 is a short, cylindrical metal element having a pointed leading end and a flat base, the suture end being attached (e.g. in known manner) at an intermediate side locality of the needle. The bore of each aperture 34 is just large enough to permit the needle to pass therethrough with minimum clearance. In transfer of a needle from the capsule 25 to the jaw 12 (FIG. 8), an advancing prong 42 of the plunger 40 engages the base of the needle within the capsule and pushes it through the clamped tissue 53, and into and entirely through the aperture 34, so that the base of the needle passes outwardly of the surface 102. As soon as the base of the needle thus emerges from the outer opening of the aperture 34, the needle (being released from the lateral confinement of the aperture wall) immediately and inherently undergoes some degree of lateral displacement. This displacement, illustrated in a somewhat exaggerated manner in FIG. 13, involves slight lateral forward movement of the needle base over the surface 102. The needle is then prevented from re-entering the aperture 34 by interference between the needle base and the surface 102, especially because of the close correspondence between the diameters of the needle and the aperture. Accordingly, when the jaws are opened, it is impossible for the needles to be pulled back through the apertures; instead, they are securely carried by the jaw 12. They are, however, readily removable from the jaw 12 incident to cutting of the suture at the completion of a suture-applying operation of the instrument.

Still further features of the invention are embodied in the structure of the capsule 25 (FIGS. 4, 5 and 9). In particular, the bobbin 31, journalled (as stated) in the side walls of the capsule housing 26, comprises a central shank 110 bearing, in addition to the usual side flanges 112, a central flange or septum 114 spaced halfway between the two side flanges on the shank so as to divide the shank into two separate winding regions. A notch 116, formed in the edge of the septum 114, receives the bight of a U-shaped flexible suture 28 when the suture is reeled on the bobbin. The two legs 28a and 28b of the suture are then respectively wound on the bobbin shank on opposite sides of the septum, being prevented by the septum from crossing over or binding each other, while the side flanges of the bobbin perform their usual function of preventing the suture from slipping off the shank.

In this structure, the septum 114 with its notch 116 for holding the bight of the suture facilitates winding of the suture on the bobbin, and also maintains the wound portions of the two legs of the suture entirely separate from each other on the bobbin shank, so as to assure that the two legs will unwind evenly and at the same rate when the suture is withdrawn from the bobbin.

As described above, the body of the capsule 25 is curved laterally (FIG. 4) to conform to the lateral curvature of the jaws. Again to facilitate smooth discharge of the suture, a guide 118 is formed within the recess 26, some distance forwardly of the bobbin 31, on the concave side of the capsule curvature. The two legs of the suture, extending forwardly from the bobbin to the needles, both pass the guide on the side thereof facing the convex side of the capsule curvature. The guide serves to maintain the path of advance of the suture legs from the bobbin fairly close to a line perpendicular to the bobbin axis, as desired to prevent binding, which might occur if the legs were permitted to unwind from the bobbin at a substantial angle to the bobbin axis, i.e. at an angle corresponding to the capsule curvature. Ventilation openings 120 and 121 are provided in the bobbin and capsule walls, respectively, to prevent deleterious entrapment of air bubbles (the capsule being packed in fluid for storage, shipment and handling prior to use).

It is to be understood that the invention is not limited to the features and embodiments hereinabove specifically set forth but may be carried out in other ways without departure from its spirit.

What is claimed is:

1. A surgical suturing instrument comprising
   (a) a first jaw;
   (b) a second jaw for cooperating with the first jaw to clamp tissue to be sutured, said second jaw having a handle;
   (c) an actuator arm manipulable jointly with the handle;
   (d) means for pivotally interconnecting said jaws and said arm for angular movement relative to each other about a common axis from which said jaws extend forwardly and said handle and said arm extend rearwardly;
   (e) means, carried by said first jaw and operable by angular movement of said arm relative to said first jaw, for applying a suture to tissue clamped between the jaws; and
   (f) latch means for selectively interlocking said first jaw with said arm and with said second jaw in succession during progressive angular movement of said arm in a closing direction toward said handle, such that movement of said arm in said direction initially moves said first jaw to a tissue-clamping, closed position relative to said second jaw and thereafter operates said suture-applying means while the jaws are interlocked;
   wherein the improvement comprises:

(g) said latch means comprising a latch member pivotally mounted on said first jaw and including
   (i) a first portion for engaging said arm when said first jaw is away from said closed position to interlock said arm and said first jaw and thereby to transmit, to said first jaw, angular motion of said arm in said closing direction, and
   (ii) a second portion engageable by said second jaw for pivotally moving said latch member in a given direction to displace said first portion out of interlocking engagement with said arm as said first jaw arrives at said closed position.

2. An instrument as defined in claim 1, wherein said arm has an abutment for engaging said latch member and said first portion of said latch member has a surface engageable by said abutment, said abutment being disposed, in relation to the axis of pivotal motion of said latch member, for exerting force on said latch member surface in a direction opposing pivotal movement of said latch member in said given direction.

3. An instrument as defined in claim 2, including means for resiliently biasing said latch member in a direction opposed to said given direction.

4. An instrument as defined in claim 3, wherein said surface of said latch member has a stop projection for engaging said abutment, when said abutment bears against the surface, to limit pivotal movement of the latch member in a direction opposed to said given direction; wherein said surface is curved, in a direction away from said stop projection, for sliding engagement with said abutment as said latch member moves pivotally in said given direction; and wherein the extent of said surface, in the direction away from said stop projection, is such that said abutment becomes disengaged from said surface when said first jaw reaches said closed position.

5. An instrument as defined in claim 4, wherein said first portion of said latch member has a second surface for slidably engaging with said arm during movement of said arm in said closing direction when said first jaw is in said closed position to restrain the latch member against movement in a direction opposed to said given direction, and wherein said second portion of said latch member has a surface for engaging said second jaw when said first jaw is in said closed position to prevent movement of said first jaw away from said closed position while the latch member is restrained as aforesaid, and thereby to interlock said first and second jaws.

6. An instrument as defined in claim 5, wherein said suture-applying means comprises means in said first jaw for holding a length of flexible suture and at least one needle connected thereto with the needle supported in a position for transfer from said first jaw to said second jaw when said first jaw is in said closed position, and plunger means carried in said first jaw and operable by angular movement of said arm relative to said first jaw for pushing the needle out of said first jaw toward said second jaw through tissue clamped between said jaws; wherein said second jaw has at least one aperture positioned to receive a needle pushed out of said first jaw by said plunger means, said aperture having first and second openings respectively facing toward and away from said first jaw; and wherein said second jaw has a flat surface facing away from said first jaw and extending laterally from the second opening of said aperture; said plunger means being arranged to push a needle from said first jaw entirely through and beyond second opening of said aperture such that the needle becomes misaligned with said aperture and engages said flat surface thereby to prevent re-entry of the needle into the aperture.

7. An instrument as defined in claim 6, wherein said holding means comprises a capsule removably mounted in said first jaw for holding a length of flexible suture and a pair of needles respectively secured to opposite ends of the suture, said capsule including a rotatably mounted bobbin bearing a centrally disposed septum having a notch for engaging the midpoint of the suture, portions of the suture on opposite sides of the midpoint being wound on the bobbin on opposite sides of said septum, respectively.

8. A surgical suturing instrument comprising
(a) a first jaw;
(b) a second jaw for cooperating with the first jaw to clamp tissue to be sutured, said second jaw having at least one aperture for receiving a needle;
(c) means for pivotally interconnecting the jaws for closing and opening movement;
(d) handle means for closing and opening the jaws; and
(e) means carried by said first jaw for applying a suture to tissue clamped between the jaws, said suture-applying means including
   (i) means in said first jaw for holding a length of flexible suture and at least one needle secured thereto, with the needle supported in a position for transfer through clamped tissue to said aperture of said second jaw when the jaws are closed, and
   (ii) plunger means in said first jaw, operable by manipulation of said handle means when the jaws are closed, for pushing a needle positioned as aforesaid out of said first jaw and through clamped tissue into said aperture of said second jaw;
wherein the improvement comprises:
(f) said second jaw defining first and second openings of said aperture respectively facing toward and away from said first jaw;
(g) said second jaw further having a flat surface facing away from said first jaw and extending laterally from the second opening of said aperture; and
(h) said plunger means being arranged to push a needle from said first jaw entirely through and beyond said second opening of said aperture such that the needle becomes misaligned with said aperture and engages said flat surface thereby to prevent re-entry of the needle into the aperture.

9. An instrument as defined in claim 8, wherein said second jaw further defines a groove opening toward said first jaw and extending laterally from one side of said aperture, said groove having a depth greater than the axial extent of said aperture so as to open into said aperture throughout the length thereof from said first aperture opening to and beyond said second aperture opening, for accommodating passage of a suture attached to a needle advanced through said aperture.

10. For use with an elongated flexible suture having a pair of needles respectively secured to opposite ends thereof, suture-carrying structure comprising
(a) a capsule adapted to be removably mounted on one jaw of a forceps, said capsule having a rearwardly extending body portion forming a recess for holding said suture with an opening for discharge thereof, and a forwardly extending portion having a pair of channels for holding said needles in position for register with a pair of needle-receiving apertures in another jaw of said forceps when said capsule is mounted on said one jaw to permit transfer of said needles to said apertures upon closing of said forceps; and
- (b) a bobbin rotatably mounted in said body portion of said capsule for holding the central portion of said suture in wound condition;

wherein the improvement comprises
- (c) said bobbin having a central septum with a notch for engaging the midpoint of the suture such that portions of the suture on opposite sides of the suture are respectively wound on the bobbin on opposite sides of the septum.

11. Structure as defined in claim 10, wherein said capsule, forwardly of said bobbin, is curved laterally of a plane perpendicular to the axis of rotation of the bobbin, and further including a guide mounted in said recess forwardly of said bobbin for guiding the side portions of the suture from the bobbin along a path substantially perpendicular to said axis as the suture is unwound from the bobbin.

12. Structure as defined in claim 10, wherein said capsule has a pair of lugs respectively projecting laterally outward from opposite sides of said forwardly extending portion for mating with lugs provided on opposite sides of said one forceps jaw to hold the capsule fixed in position in said one jaw.

* * * * *

UNITED STATES PATENT AND TRADEMARK OFFICE
CERTIFICATE OF CORRECTION

PATENT NO. : 4,164,225
DATED : August 14, 1979
INVENTOR(S) : Alfred A. Johnson et al.

It is certified that error appears in the above-identified patent and that said Letters Patent are hereby corrected as shown below:

Col. 2, line 53, "surgical instrument" should read --surgical suturing instrument-- .

Col. 5, line 62, "forward of" should read --forward tip of-- .

Signed and Sealed this

Sixteenth Day of November 1982

[SEAL]

Attest:

GERALD J MOSSINGHOFF

Attesting Officer

Commissioner of Patents and Trademarks